(12) United States Patent
Matsumoto (10) Patent No.: US 10,704,072 B2
(45) Date of Patent: Jul. 7, 2020

(54) CELL CULTURE EVALUATION SYSTEM AND METHOD

(71) Applicant: FUJIFILM Corporation, Tokyo (JP)

(72) Inventor: Tsuyoshi Matsumoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 171 days.

(21) Appl. No.: 15/445,424

(22) Filed: Feb. 28, 2017

(65) Prior Publication Data

US 2017/0166948 A1 Jun. 15, 2017

Related U.S. Application Data

(63) Continuation of application No. PCT/JP2015/070197, filed on Jul. 14, 2015.

(30) Foreign Application Priority Data

Sep. 12, 2014 (JP) .................. 2014-186173

(51) Int. Cl.
*C12M 1/36* (2006.01)
*C12Q 1/02* (2006.01)
(Continued)

(52) U.S. Cl.
CPC .............. *C12Q 1/02* (2013.01); *C12M 23/12* (2013.01); *C12M 41/46* (2013.01); *C12M 41/48* (2013.01)

(58) Field of Classification Search
CPC ....... C12M 41/14; C12M 23/12; C12M 41/48
See application file for complete search history.

(56) References Cited

U.S. PATENT DOCUMENTS

2003/0040104 A1* 2/2003 Barbera-Guillem ........................ C12M 23/24
435/286.2
2014/0064594 A1 3/2014 Sugiyama et al.

FOREIGN PATENT DOCUMENTS

JP 2003-289848 A 10/2003
JP 2006-6261 A 1/2006
(Continued)

OTHER PUBLICATIONS

Extended European Search Report dated Aug. 2, 2017, for corresponding European Application No. 15839995.6.
(Continued)

*Primary Examiner* — Jonathan M Hurst
(74) *Attorney, Agent, or Firm* — Birch, Stewart, Kolasch & Birch, LLP (57) ABSTRACT

A cell culture evaluation system includes a cell culture device 10 culturing a plurality of cell culture units of which arrangements are changed; and a cell quality evaluation device 60 including a cell quality evaluation portion 61 that performs image-evaluation on qualities based on images of the cell culture units and a cell arrangement-position storage unit 64 that stores respective arrangement-positions of the cell culture units before and after the arrangement change. When portion of the cell culture units among the plurality of cell culture units are selected to be subjected to image-evaluation, if cell culture units of which results of the image-evaluation do not satisfy predetermined conditions exist, cell culture units, which have been arranged in a predetermined distance range from the cell culture units that do not satisfy the conditions, are specified and evaluated to a point of time of the image-evaluation based on the stored respective arrangement-positions.

20 Claims, 5 Drawing Sheets

(51) Int. Cl.
*C12M 1/32* (2006.01)
*C12M 1/34* (2006.01)

(56) References Cited

FOREIGN PATENT DOCUMENTS

| | | |
|---|---|---|
| JP | 2006-350740 A | 12/2006 |
| JP | 2012-231709 A | 11/2012 |
| WO | WO 2011/016189 A1 | 2/2011 |
| WO | WO 2012/115153 A1 | 8/2012 |

OTHER PUBLICATIONS

International Preliminary Report on Patentability, issued in PCT/JP2015/070197, dated Mar. 14, 2017.
Written Opinion of the International Searching Authority (PCT/ISA/237), issued in PCT/JP2015/070197, dated Aug. 11, 2015.
International Search Report (PCT/ISA/210), issued in PCT/JP2015/070197, dated Aug. 11, 2015.
Japanese Office Action and English translation thereof, dated Jun. 6, 2017, for Japanese Application No. 2014-186173.

* cited by examiner

| T0 (INITIAL STAGE) | | | T1 (PAST) | | | T2 (PRESENT) | | |
|---|---|---|---|---|---|---|---|---|
| POSITION INFORMATION OF CULTURE VESSEL | ID | RANK | POSITION INFORMATION OF CULTURE VESSEL | ID | RANK | POSITION INFORMATION OF CULTURE VESSEL | ID | RANK |
| T0-1A | 1 | A | T1-1A | 1 |   | T2-1A | 1 |   |
| T0-1B | 2 | B | T1-1B | 2 | B | T2-1B | 2 | B |
| T0-1C | 3 | B | T1-1C | 3 | B | T2-1C | 3 | C |
| T0-1D | 4 | A | T1-1D | 4 |   | T2-1D | 4 |   |
| ⋮ | ⋮ | ⋮ | ⋮ | ⋮ | ⋮ | ⋮ | ⋮ | ⋮ |
| T0-4E | 23 | A | T1-4E | 23 |   | T2-4E | 23 |   |
| T0-4F | 24 | A | T1-4F | 24 |   | T2-4F | 24 |   |

CELL CULTURE EVALUATION SYSTEM AND METHOD

CROSS-REFERENCE TO RELATED APPLICATIONS

This application is a Continuation of PCT International Application No. PCT/JP2015/070197 filed on Jul. 14, 2015, which claims priority under 35 U.S.C. § 119(a) to Japanese Patent Application No. 2014-186173 filed on Sep. 12, 2014. Each of the above application(s) is hereby expressly incorporated by reference, in its entirety, into the present application.

BACKGROUND OF THE INVENTION

1. Field of the Invention

The present invention relates to a cell culture evaluation system that cultures a plurality of cell culture units while arrangements of the plurality of the cell culture units are changed and evaluates qualities of the cell culture units, and a method.

2. Description of the Related Art

Recently, regenerative medicine that performs treatments by culturing cells such as skins, retinae, and myocardia in a sheet shape and transplanting these to a patient attracts attention. It is considered to culture cells to be used in regenerative medicine such as blood cells and nerves.

In order to produce cell sheets such as skins, first, a small amount of cells are gathered from a living body, the gathered cells are derived to undifferentiated cells such as iPS cells, and the obtained undifferentiated cells are cultured. The cell sheets are produced by differentiating and deriving the obtained cells in a skin cell and arranging and culturing the differentiated and derived cells in a sheet shape.

Meanwhile, as described above, when the cells are cultured, it is important that qualities of the cells are evaluated and managed. Therefore, images of the cells are picked up and qualities of the cells are evaluated based on the images. For example, WO2011/016189A suggests determining maturity of cells based on images obtained by picking up images of cells. JP2006-350740A suggests observing changes of cells with time by picking up images of cells in a time series.

SUMMARY OF THE INVENTION

Here, in a case where a cell sheet is cultured as described above, the number of cells in the cell sheet is about $10^5$ to $10^6$ or greater, and thus is a great amount. Therefore, it is extremely difficult to pick up images of all of the cells and evaluate qualities thereof.

Therefore, it is considered that a portion of cells in the cell sheet is extracted and evaluated and, in a case where there are abnormal cells, the cells are removed. However, when the cell sheet is cultured, a plurality of cells in the cell sheet are not necessarily cultured in the same way. For example, the culture state may vary depending on the culture environment. Here, it is considered that, cells in the cell sheet are cultured while the cells are moved in a well unit or a cell colony unit. However, in a case where abnormal cells exist in the extraction evaluation described above, cells that have come into contact with the abnormal cells even once in the past may be influenced by the abnormal cells and qualities thereof may be possibly deteriorated. Cells that have been cultured in a position close to the abnormal cells in the past may also have the same qualities as the abnormal cells since the cells are cultured in the same culture environment or the cells exchange growth factors with each other. Therefore, the cells have to be removed.

Not in the cell units in the cell sheet described above, for example, even in a case where culture is performed by arranging a plurality of culture vessels in order, it is considered that culture is performed by changing arrangements of the culture vessels in order to achieve homogeneous qualities of the cultured cells in the respective culture vessels. Also in this case, as described above, in a case where, for example, a culture vessel including abnormal cells exists, cells in the culture vessel that are cultured near the culture vessel in the past may be possibly abnormal.

According to the invention, in view of the above, an object of the invention is to provide a cell culture evaluation system that cultures a plurality of cell culture units while arrangement of the plurality of cell culture units are changed and evaluates qualities of the cell culture unit and a method thereof, in which abnormal cell culture units can be suitably found even in a case where the extraction evaluation is performed.

A cell culture evaluation system according to the invention includes: a cell culture device that cultures a plurality of cell culture units of which arrangement is changed; a cell quality evaluation device including a cell quality evaluation portion that performs image evaluation on qualities of the cell culture units based on images of the cell culture units and a cell arrangement position storage unit that stores respective arrangement positions of the plurality of cell culture units before and after the arrangement change, in which, when the cell quality evaluation portion selects a portion of the cell culture units among the plurality of cell culture units and performs image evaluation, in a case where cell culture units that do not satisfy predetermined conditions exist in the portion of the cell culture units as a result of the image evaluation, the cell quality evaluation portion specifies cell culture units that have been arranged in a predetermined distance range from the cell culture units that do not satisfy the conditions to a point of time of the image evaluation based on the respective arrangement positions stored in the cell arrangement position storage unit and evaluates the specified cell culture units.

The cell culture evaluation system according to the invention may include an evaluation result storage unit that stores information on results of the image evaluation of the cell culture units.

The evaluation results stored in the evaluation result storage unit may be displayed on a display apparatus.

When the cell quality evaluation portion performs image evaluation on all of the cell culture units and thereafter performs image evaluation again, cell culture units with relatively better evaluation results are removed from cell culture units to be evaluated.

An identification information providing unit that respectively provides identification information to the plurality of cell culture units may be included, and the cell arrangement position storage unit may store arrangement positions of the plurality of cell culture units by storing the identification information provided to the cell culture units.

The cell quality evaluation portion previously performs image evaluation on cell culture units arranged in the distance range at a point of time temporally closer to a point of time at present among the cell culture units that have been arranged in the predetermined distance range in the past, and, in a case where all of the cell culture units arranged in the distance range at a first point of time in the past satisfy the conditions as a result of the image evaluation, image evaluation on the cell culture units arranged in the distance range at a second point of time before the first point of time may not be performed.

Evaluation standards when the cell quality evaluation portion evaluates the cell culture units arranged in the distance range at a temporally closer point of time among the cell culture units that have been arranged in the predetermined distance range in the past may be set to be relatively higher than evaluation standards when the cell quality evaluation portion evaluates cell culture units arranged in the distance range at a temporally farther point of time.

A culture condition history storage unit that stores histories of culture conditions in the cell culture device may be included.

Histories of the culture conditions stored in the culture condition history storage unit may be displayed.

The cell culture device may include a plurality of culture portions, and it is preferable that the plurality of cell culture units are cultured in the plurality of culture portions.

It is preferable that culture conditions of the plurality of culture portions are different from each other.

It is preferable that the cell culture units are used for forming tissues, blood cells, or nerves that are cultured in a sheet shape.

The cell culture device may have an arrangement position change portion that changes arrangement positions of the cell culture units.

The arrangement positions stored in the cell arrangement position storage unit may be displayed on a display apparatus.

A cell culture evaluation method according to the invention includes: culturing a plurality of cell culture units while arrangements of the plurality of the cell culture units are changed and storing respective arrangement positions before and after the arrangement change of the plurality of cell culture units; and selecting a portion of the cell culture units among the plurality of cell culture units, when image evaluation is performed on qualities of the cell culture units based on images of the cell culture units, in a case where cell culture units that do not satisfy predetermined conditions exist in the portion of the cell culture units as a result of the image evaluation, specifying cell culture units that have been arranged in a predetermined distance range from the cell culture units that do not satisfy the conditions to a point of time of the image evaluation based on the stored respective arrangement positions, and evaluating the specified cell culture units.

In the cell culture evaluation system and the cell culture evaluation method according to the invention, when a portion of the cell culture units among the plurality of cell culture units is selected and image evaluation is performed, in a case where cell culture units that do not satisfy predetermined conditions exist in the portion of the cell culture units as a result of the image evaluation, cell culture units that have been arranged in a predetermined distance range from the cell culture units that do not satisfy the conditions to a point of time of the image evaluation are specified based on the respective arrangement positions of the stored cell culture units, and the specified cell culture units are evaluated. Therefore, even in a case where the extraction evaluation is performed, abnormal cell culture units can be suitably found.

DESCRIPTION OF THE PREFERRED EMBODIMENTS

Figure 1:
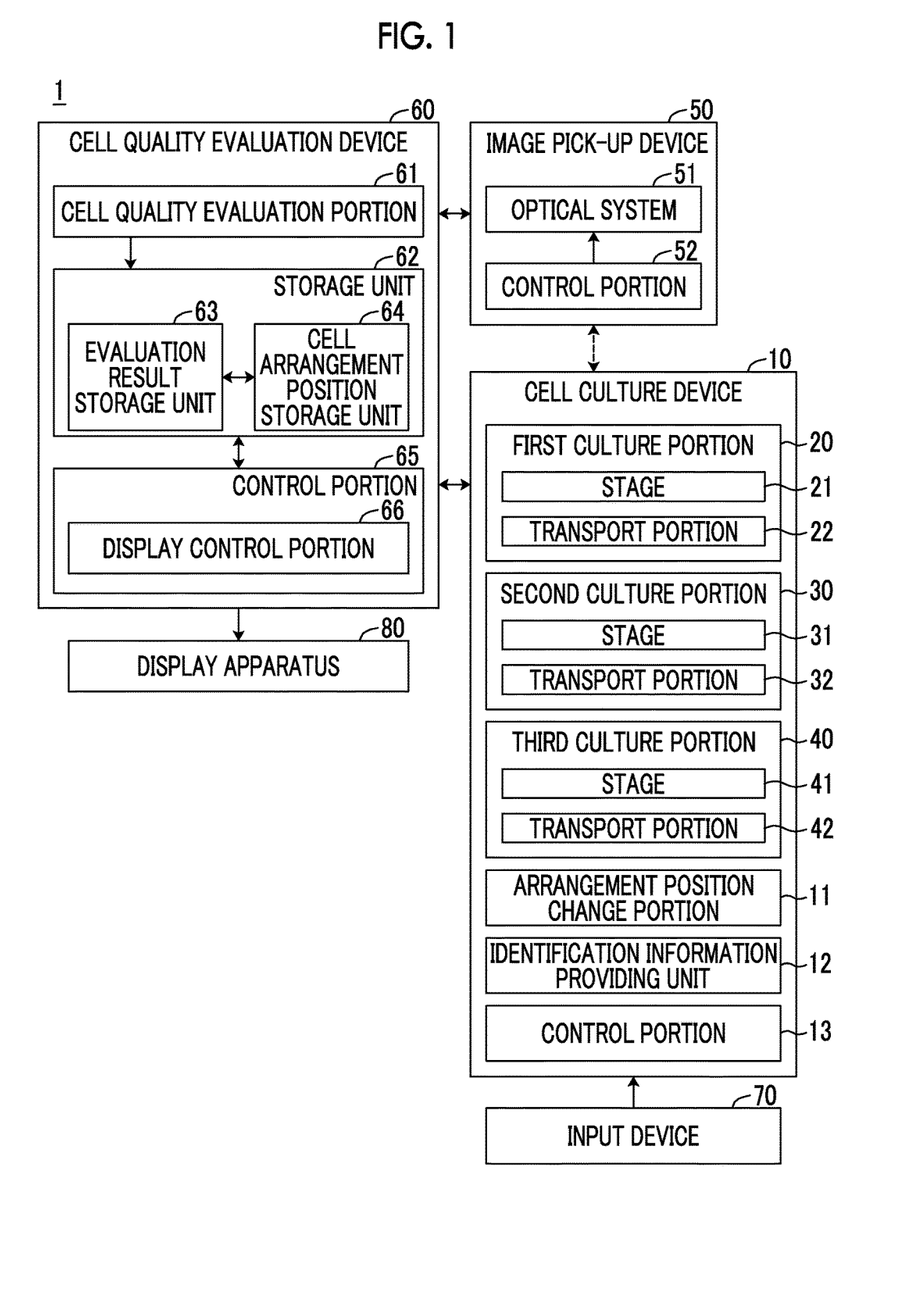
FIG. 1 is a block diagram schematically illustrating a configuration of a cell culture evaluation system according to an embodiment of the invention.

Hereinafter, an embodiment of a cell culture evaluation system according to the invention is described with reference to the drawings. FIG. 1 is a block diagram schematically illustrating a configuration of a cell culture evaluation system 1 according to the embodiment.

As illustrated in FIG. 1, the cell culture evaluation system 1 according to the embodiment includes a cell culture device 10, an image pick-up device 50, a cell quality evaluation device 60, an input device 70, and a display apparatus 80.

The cell culture device 10 includes first to third culture portions 20, 30, and 40, an arrangement position change portion 11, an identification information providing unit 12, and a control portion 13.

The first to third culture portions 20, 30, and 40 culture cells. Examples of the cells to be cultured include cells cultured in a sheet shape such as skins, retinas, and myocardia and cells that form blood cells, nerves, and organs. Pluripotent stem cells called iPS cells and ES cells may be cultured.

One or a plurality of culture vessels in which cells to be cultured are seeded on culture media are stored in the respective culture portions 20, 30, and 40. Since basic configurations of the first to third culture portions 20, 30, and 40 according to the embodiment are the same, the configuration of the first culture portion 20 is mainly described. The first culture portion 20 includes a stage 21 and a transport portion 22.

Figure 2:
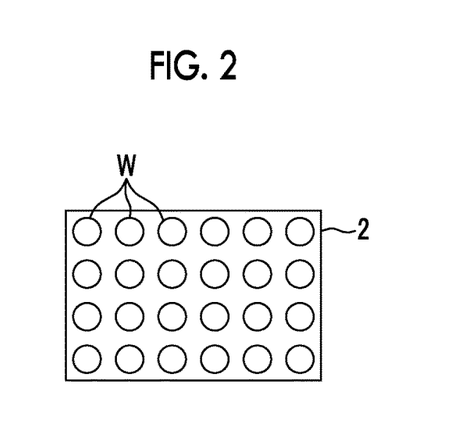
FIG. 2 is a diagram illustrating an example of a culture vessel.

In the stage 21, a culture vessel in which cells to be cultured are seeded is installed. FIG. 2 illustrates an example of a culture vessel 2 used in the embodiment. As illustrated in FIG. 2, the culture vessel 2 used in the embodiment is a well plate including 24 wells W in four rows and six columns. A culture medium and one or a plurality of colonies of cells to be cultured are stored in each of the wells W, and thus the cell colonies are cultured in the respective wells W. In the embodiment, the respective wells W correspond to cell culture units. The stage 21 may include a mechanism that shakes the culture vessel 2.

When images of cell colonies in respective wells in the culture vessel 2 is picked up by the image pick-up device 50, the transport portion 22 transports the culture vessel 2 from the first culture portion 20 to an image pick-up position in the image pick-up device 50. Specific configurations of the transport portion 22 may be, for example, a configuration of including a rotation stage and a driving mechanism that rotates the rotation stage and transporting the culture vessel 2, which is moved from the stage 21 to the rotation stage, to the image pick-up device 50 by rotating the rotation stage by a driving mechanism, a configuration of including a transporting belt and a driving mechanism thereof and transporting the culture vessel 2 to the image pick-up device 50 by the transporting belt, and a configuration of including a transporting robot and transporting the culture vessel 2 to the image pick-up device 50 by the transporting robot.

With respect to the second culture portion 30 and the third culture portion 40, basic configurations thereof are the same as that of the first culture portion 20 as described above. That is, configurations of the stages 21, 31, and 41 are the same with each other and configurations of the transport portions 22, 32, and 42 are the same with each other.

The arrangement position change portion 11 changes arrangement positions of the respective wells W in the culture vessels 2 in the first to third culture portions 20, 30, and 40. The arrangement positions of the respective wells W may be changed in one culture vessel 2 in any one of the culture portions and may be changed between the respective culture vessels 2 in the respective culture portions 20, 30, and 40. The change of the arrangements of the wells W means not only the change of arrangements of the wells W but also the change of arrangements in units of the wells W, including a case where an arrangement of a cell colony in a predetermined well W is changed to another well W.

With respect to a method of changing arrangement positions of the respective wells W, a user may instruct and input a change of an arrangement position by using the input device 70 and arrangement positions may be automatically changed based on a predetermined arrangement change rule. The information on the changes of the arrangement positions of the wells W by the arrangement position change portion 11 is output to the cell quality evaluation device 60 and is stored in a cell arrangement position storage unit 64.

As the specific configuration of the arrangement position change portion 11, for example, the arrangement position change portion 11 may include a robot arm and select and move a well with the robot arm. As the methods of moving the respective wells, in a case of a configuration in which the respective wells W of the culture vessels 2 can be detached, the wells may be grabbed and moved by the robot arm, or cell colonies in the respective wells W are sucked by a sucking mechanism together with a culture medium and the sucked cell colonies may be moved to other wells W by the robot arm.

The identification information providing unit 12 provides identification information with respect to the respective cell culture units. Specifically, the identification information providing unit 12 of the embodiment provides identification information to the respective wells W of the culture vessels 2 in the first to third culture portions 20, 30, and 40. The identification information is information for identifying the respective wells W of the respective culture vessels 2. Specifically, different ID numbers are respectively provided to the respective wells W of the respective culture vessels 2. The ID numbers of the respective wells W and arrangement position information in the culture vessels 2 of the wells W can be always associated with each other, and in a case where a position of a predetermined well W is changed by the arrangement position change portion 11, the arrangement position information after the change and the ID numbers of the wells W are associated with each other, association relationships are output to and stored in the cell arrangement position storage unit 64 of the cell quality evaluation device 60.

The control portion 13 controls the entire cell culture device 10 and controls the culture conditions in the first to third culture portions 20, 30, and 40. Specifically, the control portion 13 controls culture conditions such as temperatures, humidity, illuminance of light source, oxygen concentrations, and carbon dioxide concentrations in the first to third culture portions 20, 30, and 40, shaking conditions of the stages 21, 31, and 41, and the like. With respect to configuration of adjusting these culture conditions, well-known configurations can be used. Respective culture conditions of the first to third culture portions 20, 30, and 40 may be the same culture conditions or may be different culture conditions.

Here, for example, even if culture conditions of the first to third culture portions 20, 30, and 40 are controlled to be the same, qualities of the cell colonies cultured by the respective culture portions 20, 30, and 40 are not necessarily the same, since maturity is different depending on cell colonies. For example, in a case where cell colonies cultured in the respective culture portions 20, 30, and 40 are arranged in order, it is required to make qualities of cell colonies homogeneous. Therefore, culture conditions such as culture starting times or culturing speeds of the respective first to third culture portions 20, 30, and 40 may be varied, and cell colonies are moved between respective culture portions while culture states of the cell colonies cultured in the respective culture portions 20, 30, and 40 are observed.

The control portion 13 controls movements of the transport portions 22, 32, and 42 or the arrangement position change portion 11.

The image pick-up device 50 picks up images of the respective wells W of the culture vessels 2. The image pick-up device 50 includes an optical system 51 that picks up images of the respective wells W and outputs image signals and a control portion 52 that controls the optical system 51.

The optical system 51 includes a microscope such as a phase contrast microscope, a differential interference microscope, or a bright field microscope. These microscopes include image pick-up elements such as complementary metal-oxide semiconductor (CMOS) sensors or charge-coupled device (CCD) sensors and image signals obtained by picking up images of the inside of the respective wells W by these image pick-up elements are output.

The control portion 52 controls the entire image pick-up device 50. For example, the control portion 52 controls changes of image pick-up positions or optical magnifications of the optical system 51 when images of the respective wells W in the culture vessels 2 are picked up.

The cell quality evaluation device 60 includes a cell quality evaluation portion 61, a storage unit 62, and a control portion 65.

The cell quality evaluation portion 61 performs image evaluation on qualities of cell colonies in the wells W based on the image signals of the respective wells W output from the image pick-up device 50. For example, evaluation of a quality of a cell colony means evaluation of a degree of goodness or badness of a cell such as activities, concentration degrees, or maturities of a cell in a cell colony.

Specifically, the cell quality evaluation portion 61 specifies a cell colony included in an image obtained by picking up an image of the well W, measures distribution states or exterior shapes of cells such as circularity of a shape of the cell colony, the number of cells in the cell colony, density of cells, and concentration degrees of the cells, a growth speed of cells in a cell colony, a movement speed, and a size of a cell colony, and uses at least one of these values, so as to obtain an evaluation value of a quality of the cell colony in the well W. As a method of specifying a cell colony, for example, the picked up image may be binarized by using a threshold value of brightness, so as to specify a cell colony. However, other well-known methods may be used. As described above, the respective wells W according to the embodiment correspond to cell culture units according to the invention. Accordingly, the cell quality evaluation portion 61 according to the embodiment obtains evaluation values in a unit of the well W.

For example, in a case where a plurality of cell colonies are included in one well W, the cell quality evaluation portion 61 may obtain an average value, a maximum value, a minimum value, a median value, or the like of the evaluation values of the plurality of cell colonies as an evaluation value. However, in a case where the respective wells W are used as cell culture units as in the embodiment, it is desirable to seed one cell colony in each of the wells W. In a case where the plurality of cell colonies are seeded, it is preferable that the plurality of cell colonies are seeded in an arrangement in which the cell colonies do not be bound to each other, in view of accuracy of image evaluation of the qualities.

With respect to the cell quality evaluation portion 61, in a case where the number of cells in the cell colony or density thereof is obtained as an evaluation value, for example, the number of cells may be counted by paying attention to nuclei or nucleoli included in the cells. At this point, for example, the number of cells may be counted by limiting the cells to cells each having one nucleus, cells each having a plurality of nuclei, or cells having nucleoli.

In a case where the growth speed of the cells is obtained as an evaluation value, the numbers of cells included in two images obtained by picking up images of the same well in a time series are respectively counted and the difference of the numbers of cells included in the two images is divided by an image pick-up interval, so as to obtain the growth speed of the cells.

In a case where the movement speeds of the cells is obtained as an evaluation, for example, with respect to respective cells included in the two images obtained by picking up images of the same wells in a time series, the same cells are associated with each other by using pattern matching or the like, linear movement distances between the associated cells are divided by image pick-up intervals, movement speeds of the respective cells are calculated, and average values, maximum values, minimum values, median values, or the like of the movement speeds of the respective cells is obtained as evaluation values.

In a case where evaluation values are obtained based on shapes of the cells, circularity of the respective cells is calculated, and average values, maximum values, minimum values, median values, or the like of the circularity may be obtained as an evaluation value. In addition to the circularity, shape patterns of the cells for each type of the cells to be cultured are stored in advance, similarity between the respective cells in the images and the shape patterns is calculated, average values, maximum values, minimum values, median values, or the like of the similarity may be obtained as evaluation values. The type information on cells to be cultured may be set and input, for example, by a user.

In a case where the sizes of the cell colonies are obtained as evaluation values, for example, areas, perimeters, maximum diameters, and the like of the cell colonies can be obtained.

With respect to the shapes of the cell colonies, in addition to the circularity, shape patterns of the cell colonies are stored in advance for each type of cells to be cultured, similarity between the shapes of the cell colonies specified from the images and the shape patterns is calculated, and the similarity is obtained as an evaluation value. The type information on the cells to be cultured may be set and input, for example, by a user.

For example, textures such as brightness, evenness, or roughness of the images of the cell colonies may be obtained as evaluation values. For example, if the maturity of the cells proceeds, concentration degrees of the cells increase, further cells are laminated, and the brightness of the images gradually increase. Accordingly, the brightness is higher, the maturity progresses.

In a case where the maturity progresses and stem cells grow as described above and become a laminated state, the evenness of the images increases and a smooth image having small irregularity can be obtained. Therefore, as the evenness of the image is higher or the image is smoother, the maturity progresses. As a method of obtaining feature amounts of the evenness or the smoothness of the image, well-known methods can be used.

A halo that is generated in a cell colony is detected and the evaluation values may be obtained based on the detected halo. The halo is generated due to diffracted light that passes between cells. The halo is seen as a white streak in the image. Accordingly, the halo is detected in the image by detecting this white streak. As a method of detecting the white streak, well-known methods can be used. For example, a pixel having a brightness value which is a predetermined threshold value or greater may be detected, or a white line may be detected by a filter treatment or the like.

For example, the number of pixels of white streaks in the cell colony is calculated, and the number of pixels of white streaks may be obtained as an evaluation value. In this case, as the number of pixels of white streaks is greater, it is considered that the concentration degree of the cells is low, and the quality of the cell colony is bad. Not the number of pixels of white streaks, but a value that indicates spatial distribution such as a density of pixels of the white streaks may be obtained as an evaluation value. In this case, since the pixels of the white streaks are localized, it is considered that the quality of the cell colony is bad. A histogram is formed with the number or the density of the white streak pixels for each local region in the cell colony, and spatial distribution may be interpreted based on this histogram.

As described above, the cell quality evaluation portion 61 ranks the respective wells W based on the calculated evaluation value, and the information of the rank is provided to the respective wells W. Specifically, the cell quality evaluation portion 61 gradually ranks the respective wells W from those having great evaluation values by performing threshold value determination on the evaluation values. According to the embodiment, ranking is performed in three stages of an A rank, a B rank, and a C rank in an order that an evaluation value is great. The cell quality evaluation portion 61 outputs rank information provided to the respective wells W, to an evaluation result storage unit 63 of the storage unit 62. The rank information obtained by the cell quality evaluation portion 61 is stored in a state in which the ID numbers of the wells W and the arrangement position information of the wells W are associated with each other.

The quality evaluation in the cell quality evaluation portion 61 is performed periodically, at a timing that is designated by a user, or the like. However, according to the embodiment, with respect to the initial quality evaluation after the start of the culture, qualities of cell colonies in all of the wells W in the culture vessels 2 are evaluated.

However, with respect to the quality evaluation thereafter, not all of the wells W but only a portion of the wells W is extracted and subjected to quality evaluation. Time for quality evaluation can be reduced by performing quality evaluation on only a portion of the wells W among the wells W in the culture vessels 2 in this manner. According to the embodiment, in the initial quality evaluation after the start of the culture as described above, qualities of the cell colonies of all of the wells W are evaluated. However, a portion of the wells W is extracted from the initial quality evaluations, and quality evaluation may be performed.

However, when qualities of a portion of the wells W are evaluated, the cell quality evaluation portion 61 in a case where the wells W that do not satisfy a predetermined condition exist in the portion of the wells W as a result of the evaluation, the wells W that have been arranged in a predetermined distance range from the wells W that do not satisfy this condition until a point of time of the evaluation at this time are specified, quality evaluation of the specified wells W is additionally performed. The cell quality evaluation portion 61 specifies the wells W to be additionally evaluated based on the arrangement position information of the respective wells W which is stored in the cell arrangement position storage unit 64, and the specification method is described below.

Figure 3:
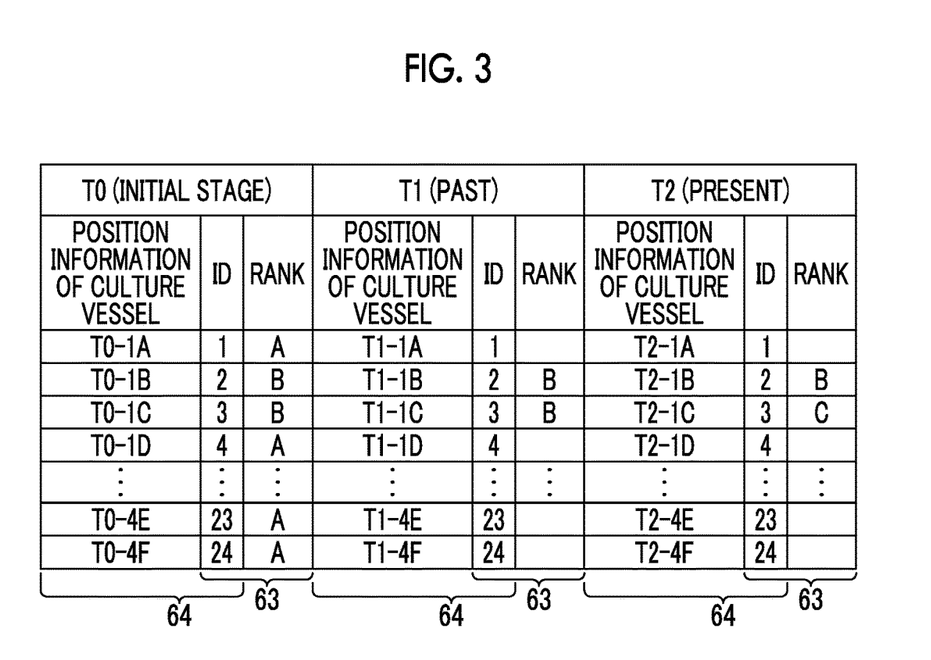
FIG. 3 is a diagram illustrating an example of a table in which evaluation results of cell culture units and arrangement position information are stored.

The storage unit 62 includes the evaluation result storage unit 63 and the cell arrangement position storage unit 64. FIG. 3 is a diagram illustrating a table including both of the evaluation result storage unit 63 and the cell arrangement position storage unit 64. According to the embodiment, the evaluation result storage unit 63 and the cell arrangement position storage unit 64 are included as one table, but may be included as different tables.

As illustrated in FIG. 3, the evaluation result storage unit 63 is stored in a state in which the rank information of the wells W output from the cell quality evaluation portion 61 and the ID numbers of the wells W are associated with each other. As described above, the quality evaluation of the respective wells W is performed periodically, at a timing that is instructed by a user, or the like, during a period of time from the start of the culture until the end of the culture. Therefore, the evaluation result storage unit 63 stores rank information for each evaluation timing thereof.

Figure 5:
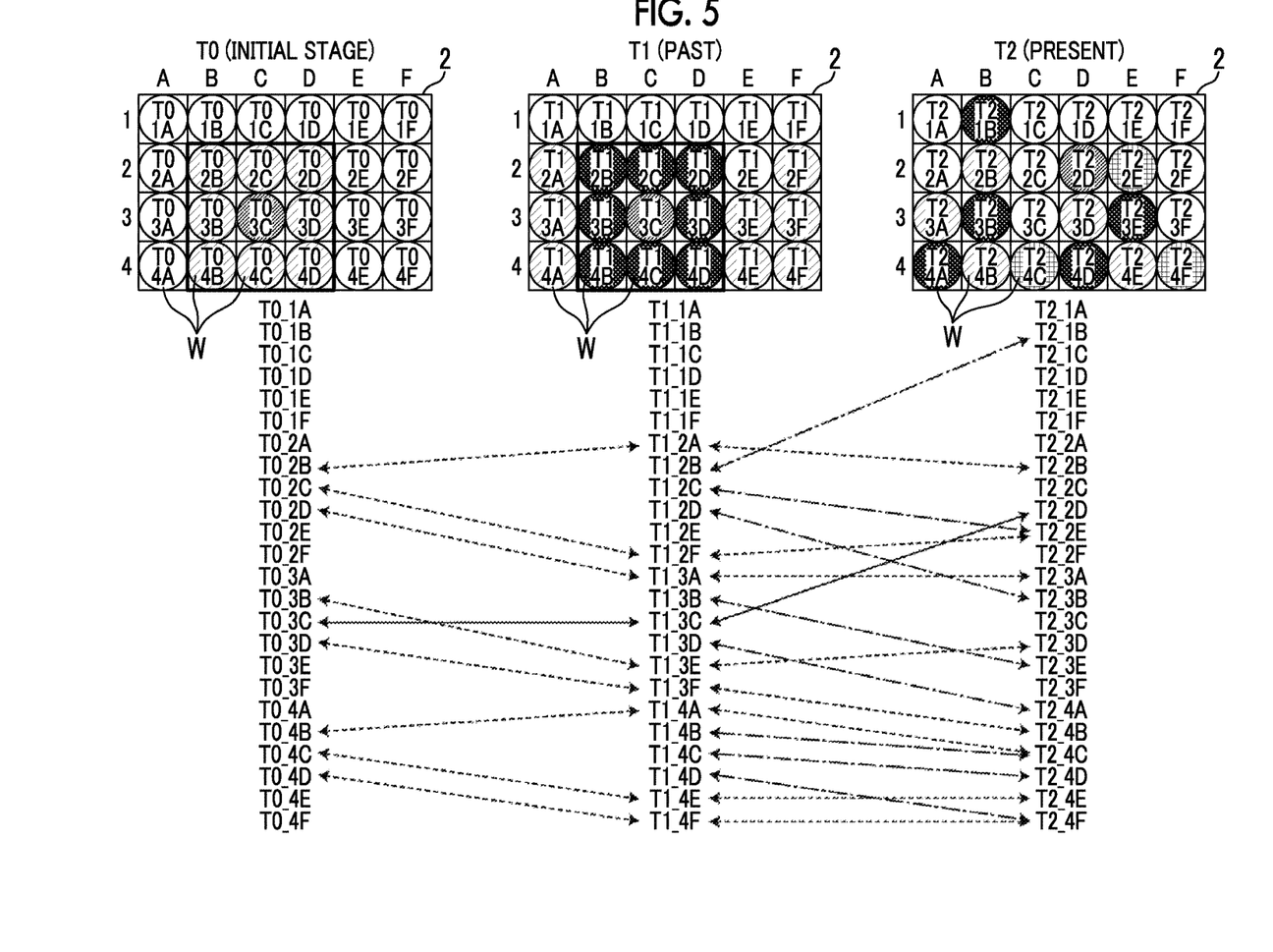
FIG. 5 is a diagram illustrating an example of movements of cell culture units in a course of culture.

The cell arrangement position storage unit 64 stores arrangement position information of the respective wells W output from the arrangement position change portion 11 of the cell culture device 10. Specifically, as illustrated in FIG. 3, the cell arrangement position storage unit 64 associates the position information of the respective wells W in the culture vessels 2 (T0_1A, T0_1B, T0_1C, T0_1D, . . . ) and the ID numbers of the wells W arranged at the positions (1, 2, 3, 4, . . . ) with each other and stores the position information and the ID numbers associated with each other as arrangement position information. The change of arrangements of the respective wells W in the culture vessels 2 is performed several times periodically or at a timing that is instructed by a user during a period of time from the start of the culture until the end of the culture. Therefore, the cell arrangement position storage unit 64 stores arrangement information of the respective wells W for each arrangement change timing thereof. The position information of the respective wells W of the culture vessels 2 illustrated in FIG. 3 is position information of the respective wells W of the culture vessels 2 at respective points of time illustrated in FIG. 5. However, FIG. 5 is described below.

The table illustrated in FIG. 3 presents arrangement position information and rank information of the respective wells W at three points of time: a present T2, a past T1 before the present, and an initial stage T0 before the past T1 and after the start of the culture, but this is an example. A timing of changing an arrangement position of the wells W of the culture vessels 2 and a timing of extraction evaluation of the portion of the wells W described above may be the same or may be different from each other.

The control portion 65 controls the entire cell quality evaluation device 60. The control portion 65 includes a display control portion 66. The display control portion 66 causes the display apparatus 80 to display the image picked up in the image pick-up device 50 and causes the display apparatus 80 to display results of quality evaluation in the cell quality evaluation portion 61 and arrangement position information of the respective wells W. The display apparatus 80 is formed by a display device such as a liquid crystal display.

The input device 70 includes a mouse, a keyboard, and the like and receives a setting input by a user. The input device 70 according to the embodiment receives an input of the change of the arrangement position of the respective wells W or receives an input of the change of culture conditions in a case where culture conditions of the first to third culture portions 20, 30, and 40 are changed.

Figure 4:
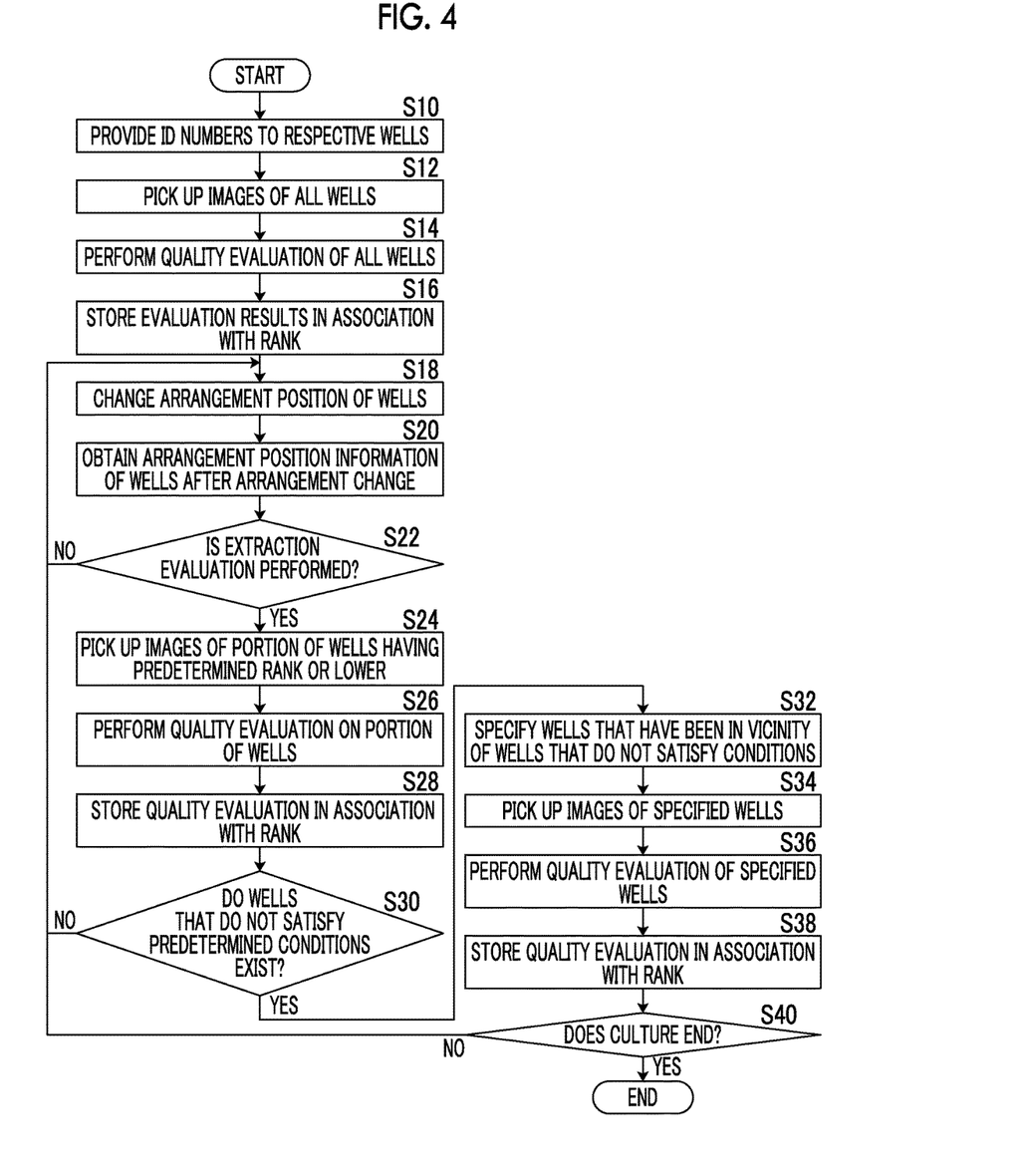
FIG. 4 is a flow chart for describing operations of the cell culture evaluation system according to the embodiment of the invention.

Subsequently, operations of the cell culture evaluation system 1 according to the embodiment are described with reference to a flow chart illustrated in FIG. 4. The cell culture evaluation system 1 according to the embodiment is characterized in additional evaluation at the time of extraction evaluation, and this point is mainly described. The cell culture evaluation system 1 according to the embodiment has the first to third culture portions 20, 30, and 40 described above and the culture vessels 2 are installed in the respective culture portions. Here, a case where qualities of the cell colonies that are cultured in the culture vessels 2 installed in any one culture portion are evaluated is described.

First, cell colonies are respectively seeded in the respective wells W of the culture vessels 2, and culture starts. ID numbers are provided to the respective wells W at the initial stage (stage in which the wells W are not moved) (S10). The ID numbers provided to the respective wells W are output to the cell arrangement position storage unit 64 and stored as initial arrangement position information associated with position information of the wells W of the culture vessels 2 (T0_1A, T0_1B, T0_1C, T0_1D, . . . , T0_4F) (see FIG. 5).

Subsequently, initial quality evaluation after the start of the culture is performed. According to the embodiment, in this initial quality evaluation, quality evaluation is performed on all of the 24 wells W in the culture vessels 2. Specifically, first, the culture vessels 2 is transported to the image pick-up device 50 by the transport portion, and the image pick-up device 50 picks up the images of all of the wells W in the culture vessels 2 (S12).

The image signals of all of the wells W are respectively output from the image pick-up device 50 and are input to the cell quality evaluation portion 61. The cell quality evaluation portion 61 evaluates the respective wells W as described above based on the image signals of the input respective wells W, provides the rank information to all of the wells W, associates the ID numbers of all of the wells W and this rank information, and stores this associated information in the evaluation result storage unit 63 (S14, S16).

Subsequently, in the stage in which a predetermined culture period has elapsed, arrangement positions of the predetermined wells W in the culture vessels 2 are changed automatically or by an instruction from a user by the arrangement position change portion 11 (S18). In a case where the arrangement position of the wells W is changed by the arrangement position change portion 11, the ID numbers of the wells W of which arrangements are changed by the arrangement position change portion 11 and position information after the arrangement change are obtained, output to the cell arrangement position storage unit 64, and stored (S20). The wells W are moved a plurality of times until the end of the culture, but the ID numbers of the wells W of which the arrangement is changed by the arrangement position change portion 11 and position information after the arrangement change are obtained each time, output to the cell arrangement position storage unit 64, and are stored (S20). For example, FIG. 3 illustrates an example of arrangement position information in a case where at a point of time T1 in the past, the well W having an ID number 2 is moved from a position of T0_1B to a position of T1_1C in the culture vessel 2 and the well W having an ID number 3 is moved from a position of T0_1C to a position of T1_1B in the culture vessel 2.

In the predetermined timing after the start of the culture, extraction quality evaluation described above is performed automatically or by an instruction from a user (S22, YES). At the time of extraction quality evaluation, the control portion 65 of the cell quality evaluation device 60 refers to rank information of the respective wells W stored in the evaluation result storage unit 63 and obtains ID numbers of the wells W having B ranks or lower among A ranks to C ranks. The control portion 65 refers to the cell arrangement position storage unit 64 and obtains position information of the ID numbers of the wells W having B ranks or lower, and outputs this position information to the control portion 52 of the image pick-up device 50. For example, in the example of FIG. 3, since results of the quality evaluation of the wells W having the ID number 2 and the ID number 3 at the point of time of the initial stage T0 are B ranks, position information T0_1B of the well W having the ID number 2 and position information T0_1C of the well W having the ID number 3 are obtained by the control portion 65 and output to the control portion 52 of the image pick-up device 50.

The control portion 52 picks up only images of the wells W having B ranks or lower based on the input position information of the wells W having B ranks or lower (S26). At this point, the images of the wells W having the A rank may not be picked up. In a case where the wells W having B ranks or lower do not exist, a portion of the wells W among the wells W having A ranks is selected and images of the selected wells W are picked up. Dispersibility of the selected wells W having A ranks is desirably a predetermined threshold value or greater.

The image signals of a portion of the wells W are respectively output from the image pick-up device 50 and input to the cell quality evaluation portion 61. The cell quality evaluation portion 61 performs quality evaluation of the respective wells W based on the input image signal of the respective wells W, provides the rank information, associates the rank information and the ID numbers, and stores the associated information in the evaluation result storage unit 63 (S28).

As a result of the extraction evaluation described above, the wells W having C ranks exist, and the cell quality evaluation portion 61 determines whether the evaluation values of the wells W satisfy the predetermined condition (S30). Specifically, the cell quality evaluation portion 61 determines whether the evaluation values of the wells W having C ranks are the predetermined threshold value or lower and determines that the cell colonies in the wells W are abnormal in a case where the evaluation values are threshold value or lower (S30, YES). In a case where the abnormal wells W exist, the cell quality evaluation portion 61 specifies the wells W that have been arranged in a predetermined distance range from the abnormal wells W until a point of time of the extraction evaluation at this point and additionally performs quality evaluation of the specified wells W (S32).

Specifically, for example, as illustrated in FIG. 5, in the extraction evaluation at this point (T2 (present)), in a case where the well W at a T2_2D position is the abnormal well W, the cell quality evaluation portion 61 first refers to the cell arrangement position storage unit 64 and specifies the ID number of the well W at the position of T2_2D. As illustrated in FIG. 5, the well W at the position of T2_2D exists at a position of T1_3C at a point of time of the past T1. In a case where the well W at the position of T0_3C at a point of time of the initial stage T0 exists, the cell quality evaluation portion 61 obtains position information of T1_3C and T0_3C above by searching the arrangement position information in the past which has the same ID number as the ID number of the well W at the position of T2_2D.

The cell quality evaluation portion 61 obtains position information of T1_2B, T1_2C, T1_2D, T1_3B, T1_3D, T1_4B, T1_4C, and T1_4D that were adjacent to T1_3C at a point of time of T in the further past, specifies ID numbers of the wells associated with this position information, and obtains the position information of the wells W at present which are adjacent to the abnormal wells W at a point of time of the past T1 by searching position information at present which is associated with the ID number. That is, as illustrated in FIG. 5, position information of T2_1B which is a movement target of the well W of T1_2B, T2_2E which is a movement target of the well W of T1_2C, T2_3B which is a movement target of the well W of T1_2D, T2_3E which is a movement target of the well W of T1_3B, T2_4A which is a movement target of the well W of T1_3D, T2_4C which is a movement target of the well W of T1_4B, T2_4D which is a movement target of the well W of T1_4C, and T2_4F which is a movement target of the well W of T1_4D is obtained.

The cell quality evaluation portion 61 obtains position information of T0_2B, T0_2C, T0_2D, T0_3B, T0_3D, T0_4B, T0_4C, and T0_4D which are adjacent to T0_3C at a point of time of the initial stage T0, specifies the ID numbers of the wells associated with this position information, and obtains position information of the wells W at present which are adjacent to the abnormal wells W at a point of time of the initial stage T0 by searching the position information of the past T1 and the present T2 associated with ID numbers thereof. That is, in the example illustrated in FIG. 5, position information of T2_2B which is a movement target of the well W of T0_2B, T2_2E which is a movement target of the well W of T0_2C, T2_3A which is a movement target of the well W of T0_2D, T2_3D which is a movement target of the well W of T0_3B, T2_4B which is a movement target of the well W of T0_3D, T2_4C which is a movement target of the well W of T0_4B, T2_4E which is a movement target of the well W of T0_4C, T2_4F which is a movement target of the well W of T0_4D is obtained.

That is, the cell quality evaluation portion 61 specifies the wells W at positions of T2_1B, T2_2E, T2_3B, T2_3E, T2_4A, T2_4D, T2_4F, T2_2B, T2_3A, T2_3D, T2_4B, T2_4C, and T2_4E as the wells W to be subjected to the quality evaluation in addition to the extraction quality evaluation at this point.

The position information of the wells W to be additionally evaluated which are specified by the cell quality evaluation portion 61 is output to the control portion 65, and the control portion 65 outputs the input position information to the control portion 52 of the image pick-up device 50.

The control portion 52 picks up the images of the wells W to be additionally evaluated based on the position information of the wells W (S34).

The image signals of the wells W to be additionally evaluated are respectively output from the image pick-up device 50 and input to the cell quality evaluation portion 61. The cell quality evaluation portion 61 performs quality evaluation of the respective wells W based on the image signals of the input respective wells W and provides rank information, associates the rank information thereof and the ID numbers, and stores the associated information in the evaluation result storage unit 63 (S36, S38).

The wells W that were arranged in vicinity of the wells W that are determined as abnormal in the quality evaluation at this point in the past and were cultured in the same culture environment can be found by performing additional evaluation as described above. That is, at this point, it is possible to find the wells W that is possibly abnormal in the same manner as the wells W that are determined as abnormal and additionally evaluate the wells W.

In the description above, the wells W that were arranged in vicinity of the wells W determined as abnormal by quality evaluation at this point in the past are added and evaluated. However, it is possible to additionally evaluate the wells W that are adjacent at present. That is, the wells W that are positioned at T2_1C, T2_1D, T2_1E, T2_2C, and T2_3C illustrated in FIG. 5 may be additionally evaluated.

As described above, eight wells W that are adjacent to the wells W determined as abnormal are additionally evaluated, but the distance range of the wells W to be additionally evaluated is not limited thereto and may be widened, and may be arbitrarily set by the user. Four wells W that are directly adjacent to the wells W determined as abnormal in four horizontal and vertical directions may be additionally evaluated. The scope when the well to be additionally evaluated is determined is not limited to a rectangle as illustrated in FIG. 5 and may be, for example, a range of a circular shape or a rhombus shape.

With respect to the cell culture evaluation system 1 according to the embodiment, the additional evaluation is performed on all of the wells W that have been adjacent to the wells W determined as abnormal in the past, but the invention is not limited thereto. Since it is highly possible that the wells W which are adjacent to the abnormal wells W at a point of time closer to a point of time of the evaluation at this point have similar quality to the wells W that are determined as abnormal at this point, the wells W adjacent to the abnormal wells W at a point of time closer to the point of time of the evaluation at this point may be preferentially evaluated.

Specifically, for example, in a case of the example illustrated in FIG. 5, first, qualities of the wells W adjacent to the abnormal wells W at a point of time of the past T1, that is, the wells W positioned at T1_2B, T1_2C, T1_2D, T1_3B, T1_3D, T1_4B, T1_4C, and T1_4D are evaluated. In a case where the abnormal wells W having C ranks and having evaluation values of the predetermined threshold value or lower do not exist among the wells W, additional evaluation is stopped at the point of time, and additional evaluation may not be performed on the wells W that are adjacent to abnormal wells W at a point of time of the initial stage T0. Meanwhile, as a result of evaluating the wells W adjacent to the abnormal wells W at a point of time of the past T1, in a case where the abnormal wells W having C ranks and having evaluation values of predetermined threshold value or lower exist among the wells W, the wells W adjacent to the abnormal wells at a point of time of the initial stage T0, that is, the wells W positioned at T0_2B, T0_2C, T0_2D, T0_3B, T0_3D, T0_4B, T0_4C, and T0_4D may be additionally evaluated.

In the cell culture evaluation system 1 according to the embodiment, among the wells W that were adjacent to the abnormal wells W in the past, the evaluation standard at the time of evaluating the adjacent wells W at the point of time that is temporally close to the point of time of the evaluation at this time is caused to be comparatively higher than the evaluation standard at the time of evaluating the adjacent wells W at a temporally farther point of time, and can be caused to be a more strict evaluation standard.

Specifically, in a case of the example illustrated in FIG. 5, threshold values for determining whether the wells W adjacent to abnormal wells at the point of time of the past T1, that is, the wells W positioned at T1_2B, T1_2C, T1_2D, T1_3B, T1_3D, T1_4B, T1_4C, and T1_4D are abnormal may be caused to be relatively great, and threshold values for determining whether the wells W adjacent to the abnormal wells at a point of time of the initial stage T0, that is, the wells W positioned at T0_2B, T0_2C, T0_2D, T0_3B, T0_3D, T0_4B, T0_4C, and T0_4D are abnormal may be caused to be relatively small. The method of changing the evaluation standard is not limited to the method of changing the threshold value as described above. For example, the evaluation values based on the respective cell units are obtained with respect to the wells W adjacent to abnormal wells at a point of time of the past T1, and the evaluation values based on cell colony units greater than the respective cell units are obtained with respect to the wells W adjacent to abnormal wells at a point of time of the initial stage T0.

In view of finding the wells W that becomes a cause of the wells W determined as abnormal in the evaluation at this point, quality evaluation is performed in an order from the wells W adjacent to the abnormal wells W at a point of time closer to the point of time of the evaluation at this point. In a case where the wells W determined as abnormal are found, additional evaluation may be stopped at the point of time.

With respect to the cell culture evaluation system 1 according to the embodiment, the wells W determined as abnormal may be, for example, removed.

In the cell culture evaluation system 1 according to the embodiment, the display control portion 66 may read out evaluation results stored in the evaluation result storage unit 63 and may cause the display apparatus 80 to display the evaluation result. The qualities of the wells W at present can be checked by displaying the evaluation results like this, and temporal changes of the evaluation results of the respective wells W and the like can be checked.

Figure 6:
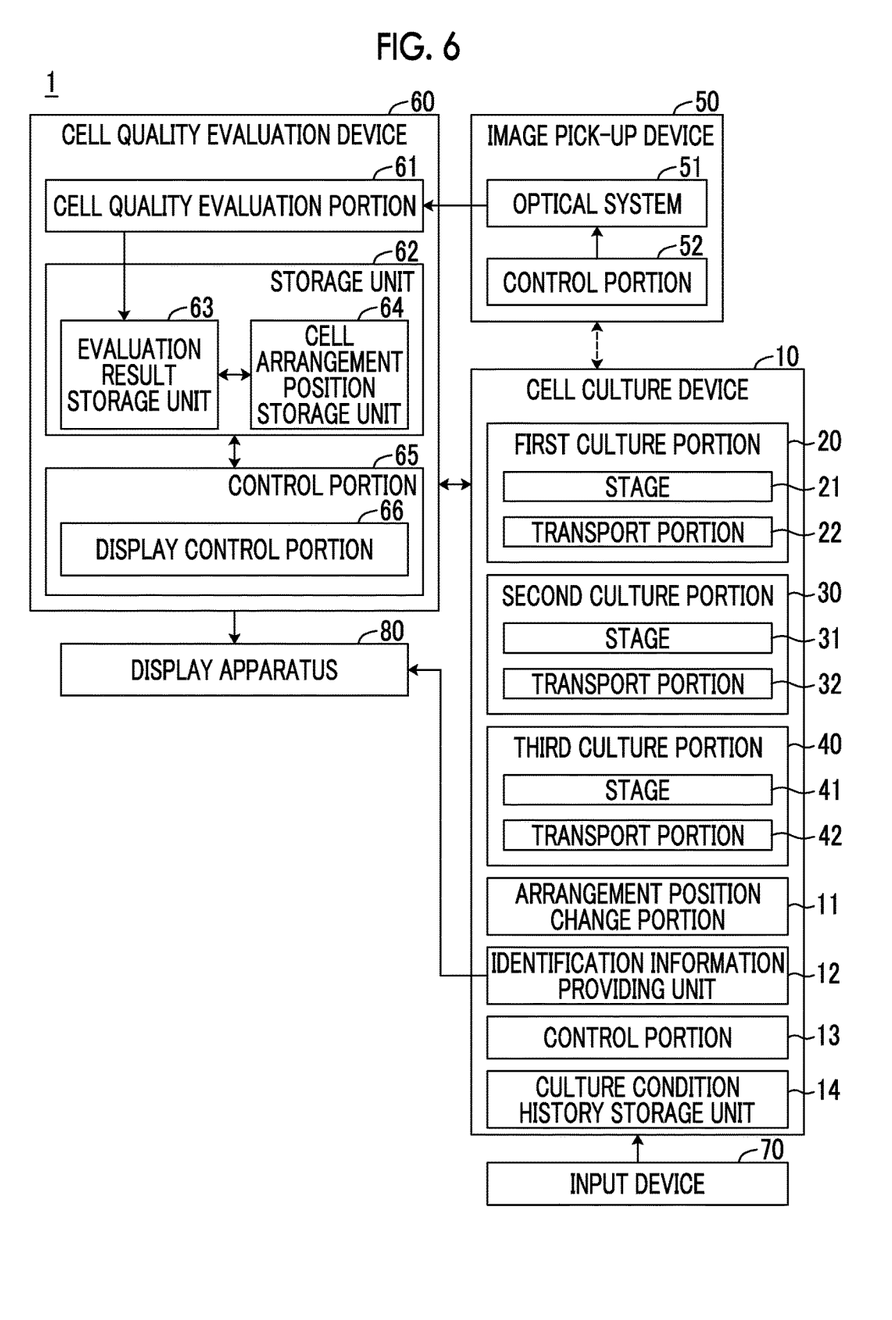
FIG. 6 is a block diagram schematically illustrating a configuration of the cell culture evaluation system illustrated in FIG. 1 in a modified example.

With respect to the cell culture evaluation system 1 according to the embodiment, in a case where the abnormal wells W exist in the quality evaluation described above, a history of the culture conditions at present or in the past is obtained, and the culture condition may be controlled based on the history of the culture condition. Specifically, as illustrated in FIG. 6, a culture condition history storage unit 14 that stores histories of the culture condition in the first to third culture portions of the cell culture device 10 may be provided such that in a case where the abnormal wells W described above exist, the control portion 13 reads out the histories of the culture conditions from the culture condition history storage unit 14 and causes the display apparatus 80 to display the histories.

For example, it is possible to cause the display apparatus 80 to display arrangement position information stored in the cell arrangement position storage unit 64, such that a user checks arrangement position information and histories of the culture conditions, checks a relationship between the arrangement positions of the abnormal wells W in the past and the culture conditions, and change the culture conditions. Specifically, the temperature unevenness of an incubator in the culture portion may be adjusted. A user does not change the culture conditions as described above, but the control portion 13 may automatically change the culture conditions. For example, in a case where the arrangement position of the abnormal wells is the same position from the start of the culture to the present, the temperature of the position, the illuminance of the light source, or the like may be adjusted.

In the description of the embodiment, respective wells of the culture vessels 2 are the cell culture units. However, for example, respective cell colonies in culture vessels or wells may be cell culture units. That is, culture is performed by changing arrangement of the plurality of cell colonies in the culture vessels or the wells, and the arrangement position information before and after the arrangement changes may be stored. In this case, ID numbers are provided to the respective cell colonies. When extraction evaluation is performed on a portion of cell colonies among the plurality of cell colonies, in a case where cell colonies that do not satisfy a predetermined condition exist as a result of the evaluation, cell colonies that have been arranged in the predetermined distance range from the cell colonies that do not satisfy the condition until the point of time of the extraction evaluation may be specified, and the specified cell colonies may be additionally evaluated. The respective cells may be cell culture units.

As the method of moving the cell colonies or the cells, for example, in a case where the culture medium is solid, the cell colonies may be removed from the culture medium by a laser and may be moved by sucking the cell colonies with a sucking mechanism. In a case where the culture medium is a liquid, the cell colonies may be moved by sucking the cell colonies with a sucking mechanism.

The culture vessels 2 may be as cell culture units. According to the embodiment, a well plate including 24 wells in four rows and six columns is used as the culture vessel 2, but the number of wells is not limited. The invention is not limited to a well plate and may be a culture vessel for suspension culture such as a pack, a flask, or a tank. In a case where suspension culture is performed, for example, images of cells that flow through a flow path connected to the culture vessel may be picked up.

EXPLANATION OF REFERENCES

1: cell culture evaluation system
2: culture vessel
10: cell culture device
11: arrangement position change portion
12: identification information providing unit
13: control portion
14: culture condition history storage unit
20: first culture portion
21: stage
22: transport portion
30: second culture portion
40: third culture portion
50: image pick-up device
51: optical system
52: control portion
60: cell quality evaluation device
61: cell quality evaluation portion
62: storage unit
63: evaluation result storage unit
64: cell arrangement position storage unit
65: control portion
66: display control portion
70: input device
80: display apparatus

What is claimed is:

1. A cell culture evaluation system comprising:
a cell culture device that cultures a plurality of cell culture units while arrangement of the plurality of cell culture units is changed, the cell culture device having an arrangement position change portion that changes arrangement positions of the cell culture units with respect to other cell culture units within the cell culture device; and
a cell quality evaluation device including a cell quality evaluation portion that performs image evaluation on qualities of the cell culture units based on images of the cell culture units and a cell arrangement position storage unit that stores respective arrangement positions of the plurality of cell culture units before and after the arrangement position change by the arrangement position change portion,
wherein, the cell quality evaluation device further includes a microprocessor configured to:
select a portion of the cell culture units among the plurality of cell culture units and performs image evaluation,
identify, based on image evaluation cell culture units in the portion of cell culture units that do not satisfy predetermined conditions;
specify cell culture units that have been arranged in a predetermined distance range from the cell culture units that do not satisfy the predetermined conditions to a point of time of the image evaluation based on the respective arrangement positions stored in the cell arrangement position storage unit and
evaluate the specified cell culture units.

2. The cell culture evaluation system according to claim 1, further comprising:
an evaluation result storage unit that stores information on results of the image evaluation of the cell culture units.

3. The cell culture evaluation system according to claim 2,
wherein results of the image evaluation stored in the evaluation result storage unit are displayed on a display apparatus.

4. The cell culture evaluation system according to claim 1,
wherein, when the cell quality evaluation portion performs image evaluation on all of the cell culture units and thereafter performs image evaluation again, cell culture units with relatively better evaluation results are removed from cell culture units to be evaluated.

5. The cell culture evaluation system according to claim 2,
wherein, when the cell quality evaluation portion performs image evaluation on all of the cell culture units and thereafter performs image evaluation again, cell culture units with relatively better evaluation results are removed from cell culture units to be evaluated.

6. The cell culture evaluation system according to claim 3, wherein, when the cell quality evaluation portion performs image evaluation on all of the cell culture units and thereafter performs image evaluation again, cell culture units with relatively better evaluation results are removed from cell culture units to be evaluated.

7. The cell culture evaluation system according to claim 1, further comprising:
an identification information providing unit that provides identification information to the plurality of cell culture units, respectively,
wherein the cell arrangement position storage unit stores arrangement positions of the plurality of cell culture units by storing the identification information provided to the cell culture units.

8. The cell culture evaluation system according to claim 2, further comprising:
an identification information providing unit that provides identification information to the plurality of cell culture units, respectively,
wherein the cell arrangement position storage unit stores arrangement positions of the plurality of cell culture units by storing the identification information provided to the cell culture units.

9. The cell culture evaluation system according to claim 3, further comprising:
an identification information providing unit that provides identification information to the plurality of cell culture units, respectively,
wherein the cell arrangement position storage unit stores arrangement positions of the plurality of cell culture units by storing the identification information provided to the cell culture units.

10. The cell culture evaluation system according to claim 4, further comprising:
an identification information providing unit that provides identification information to the plurality of cell culture units, respectively,
wherein the cell arrangement position storage unit stores arrangement positions of the plurality of cell culture units by storing the identification information provided to the cell culture units.

11. The cell culture evaluation system according to claim 1,
wherein the cell quality evaluation portion previously performs image evaluation on cell culture units arranged in the distance range at a point of time temporally closer to a point of time at present among the cell culture units that have been arranged in the predetermined distance range in the past, and, in a case where all of the cell culture units arranged in the distance range at a first point of time in the past satisfy the conditions as a result of the image evaluation, image evaluation on the cell culture units arranged in the distance range at a second point of time before the first point of time is not performed.

12. The cell culture evaluation system according to claim 1,
wherein evaluation standards when the cell quality evaluation portion evaluates the cell culture units arranged in the distance range at a temporally closer point of time among the cell culture units that have been arranged in the predetermined distance range in the past are set to be relatively higher than evaluation standards when the cell quality evaluation portion evaluates cell culture units arranged in the distance range at a temporally farther point of time.

13. The cell culture evaluation system according to claim 1, further comprising:
a culture condition history storage unit that stores histories of culture conditions in the cell culture device.

14. The cell culture evaluation system according to claim 8,
wherein histories of the culture conditions stored in the culture condition history storage unit are displayed.

15. The cell culture evaluation system according to claim 1,
wherein the cell culture device includes a plurality of culture portions, and
the plurality of cell culture units are cultured in the plurality of culture portions.

16. The cell culture evaluation system according to claim 10,
wherein culture conditions of the plurality of culture portions are different from each other.

17. The cell culture evaluation system according to claim 1,
wherein the cell culture units are used for forming tissues, blood cells, or nerves that are cultured in a sheet shape.

18. The cell culture evaluation system according to claim 1,
wherein the cell culture device has an arrangement position change portion that changes arrangement positions of the cell culture units.

19. The cell culture evaluation system according to claim 1,
wherein the arrangement positions stored in the cell arrangement position storage unit are displayed on a display apparatus.

20. A cell culture evaluation method using the cell culture evaluation system according to claim 1, comprising:
culturing a plurality of cell culture units while arrangements of the plurality of the cell culture units are changed and storing respective arrangement positions before and after the arrangement change of the plurality of cell culture units; and
selecting a portion of the cell culture units among the plurality of cell culture units, when image evaluation is performed on qualities of the cell culture units based on images of the cell culture units, in a case where cell culture units that do not satisfy predetermined conditions exist in the portion of the cell culture units as a result of the image evaluation, specifying cell culture units that have been arranged in a predetermined distance range from the cell culture units that do not satisfy the conditions to a point of time of the image evaluation based on the stored respective arrangement positions, and evaluating the specified cell culture units.

* * * * *